(12) United States Patent
Evers et al.

(10) Patent No.: US 7,758,730 B2
(45) Date of Patent: Jul. 20, 2010

(54) METHOD FOR IMPROVING A PIPERAZINE COLOUR STABILITY

(75) Inventors: Holger Evers, Mannheim (DE); Michael Jödecke, Bobenheim-Roxheim (DE); Johann-Peter Melder, Böhl-Iggelheim (DE); Gunther Van Cauwenberge, Wachenheim (DE); Jan Nouwen, Brecht (BE)

(73) Assignee: BASF Aktiengesellschaft (DE)

( * ) Notice: Subject to any disclaimer, the term of this patent is extended or adjusted under 35 U.S.C. 154(b) by 677 days.

(21) Appl. No.: 11/659,531

(22) PCT Filed: Aug. 3, 2005

(86) PCT No.: PCT/EP2005/000841

§ 371 (c)(1),
(2), (4) Date: Feb. 5, 2007

(87) PCT Pub. No.: WO2006/015780

PCT Pub. Date: Feb. 16, 2006

(65) Prior Publication Data

US 2007/0295592 A1    Dec. 27, 2007

(30) Foreign Application Priority Data

Aug. 5, 2004    (DE) .................. 10 2004 038 107

(51) Int. Cl.
*B01D 3/42* (2006.01)
*C07D 295/023* (2006.01)

(52) U.S. Cl. .................. 203/1; 203/14; 203/99; 203/DIG. 19; 544/358

(58) Field of Classification Search ............. 203/1, 203/12, 14, 99, DIG. 19; 544/358; 564/497
See application file for complete search history.

(56) References Cited

U.S. PATENT DOCUMENTS

| 3,105,019 | A | | 9/1963 | Murray et al. |
| 4,032,411 | A | * | 6/1977 | Tornquist et al. ............ 203/14 |
| 4,736,030 | A | * | 4/1988 | Mueller et al. ............ 544/374 |
| 4,911,793 | A | * | 3/1990 | Mueller et al. ............ 203/92 |
| 5,175,369 | A | * | 12/1992 | Fowlkes ............ 564/497 |
| 5,626,724 | A | * | 5/1997 | Malsch et al. ............ 203/76 |
| 5,663,444 | A | * | 9/1997 | Melder et al. ............ 524/477 |
| 5,755,975 | A | | 5/1998 | Eck et al. |
| 2007/0037980 | A1 | * | 2/2007 | Joedecke et al. ............ 544/358 |

FOREIGN PATENT DOCUMENTS

| DE | 195 36 792 | 4/1997 |
| GB | 1263588 | 2/1972 |

* cited by examiner

*Primary Examiner*—Virginia Manoharan
(74) *Attorney, Agent, or Firm*—Connolly Bove Lodge & Hutz LLP

(57) ABSTRACT

The present invention relates to a process for improving the color stability by postpurifying piperazine, the steps comprising
preparing an aqueous piperazine solution by introducing solid or liquid piperazine having a degree of purity of at least 90% by weight in water;
removing the water by distillation;
isolating the piperazine with a predefined maximum residual content of water.

The invention further provides a rapid test of aging for checking the improvement in the color stability.

20 Claims, No Drawings

METHOD FOR IMPROVING A PIPERAZINE COLOUR STABILITY

RELATED APPLICATIONS

This application is a national stage application (under 35 U.S.C. 371) of PCT/EP2005/008401 filed Aug. 3, 2005, which claims benefit of German application 10 2004 038 107.0 filed Aug. 5, 2004.

The present invention relates to a process for improving the color stability by post-purifying piperazine.

Piperazine finds use in the preparation of a wide range of pharmaceutical products for humans and animals as far as adhesives. Special requirements are therefore made on piperazine with regard to purity and quality.

In addition to the purity, determined usually by gas chromatography, and the water content, an important quality feature is the degree of discoloration and the color stability.

A measure used for the degree of discoloration is usually what is known as the color number. The color number is a characteristic value for the color of transparent substances which is measured under specified conditions and is determined by visual comparison. A color number frequently used in the case of liquids is the APHA (American Public Health Association) color number (Römpp Chemie Lexikon 1995).

So that piperazine can be obtained in the desired purity, the literature describes various purification processes. For example, the purification may be effected via the stage of the carbamates, hydrochlorides or imines.

DE-A-195 36 792 describes, for example, the separation and purification by crystallization.

In modern processes, however, piperazine is obtained in the desired purity usually in the distillative removal of a product mixture. In recent times, such high-performance distillation apparatus has become available that the piperazine fraction which is ultimately obtained already has the desired degree of purity. The distillation thus includes both the process step of the removal (isolation) and that of the purification in a single step. From an economic point of view, this constitutes a particularly efficient procedure, even though the piperazine first has to be repeatedly fractionated in one or more columns.

On the industrial scale, piperazine is usually obtained as one of the products of value in the preparation of various ethylenamines. In this case, the synthesis is based on the reaction of ethylene dichloride (EDC process) or monoethanolamine (MEOA process) with ammonia. Further coproducts of this reaction are ethylenediamine (EDA), diethylenetriamine (DETA), triethylenetetramine (TETA) and higher linear and cyclic ethylenamines, and also additionally aminoethylethanolamine (AEEA) in the MEOA process.

Both synthetic routes are based ultimately on the oxidation of ethylene (with chlorine or oxygen) to EDC and ethylene oxide (EO) respectively and subsequent one- or two-stage reaction with ammonia. Although the MEOA process thus includes an additional synthetic step, the chlorine oxidizing agent is expensive and a salt burden is additionally unavoidable.

In comparison to the EDC process, the MEOA process ensures an increased content of cyclic compounds, so that, when a piperazine-containing product mix is desired, this constitutes the preferred process.

Irrespective of the choice of process, the purification and separation of the ethylenamine product mix in industrial production is usually effected using a battery of columns in continuous operation. Initially, the ammonia is drawn off in a pressure column, then the process water which is formed (or added in the EDC process) is distilled off.

In this context, GB 1 263 588 describes the purification of the product mix by the azeotropic removal of impurities while the water is distilled off.

In contrast, U.S. Pat. No. 3,105,019 describes the addition of organic solvents as azeotroping agents for piperazine in the distillation, specifically to remove a piperazine-TEDA fraction.

Although all of the above-described processes afford piperazine or other ethylamine products or product mixtures with sufficient purity, it is not guaranteed that the products have sufficient color stability, even when the color number determined immediately after isolation corresponds to the requirements.

This is because the discoloration components generally cannot be detected as individual compounds and are below the detection limit, for example, in the gas chromatography purity check. Especially in the MEOA process, these compounds are based on acetaldehyde fragments and their condensed subsequent products. This only forms the chromophoric compounds in the course of time, so that a color change frequently occurs only after storage, with the effect that the desired specification is no longer attained.

It is thus an object of the invention to provide a process which improves the color stability of piperazine which is in itself sufficiently pure.

The object is achieved by a process for improving the color stability by postpurifying piperazine, the steps comprising
  preparing an aqueous piperazine solution by introducing solid or liquid piperazine having a degree of purity of at least 90% by weight in water;
  removing the water by distillation;
  isolating the piperazine with a predefined maximum residual content of water.

This is because it has been found that this postpurification of piperazine with sufficient purity of 90% by weight, as can be achieved readily in customary distillation processes, allows the color stability to be improved.

The process serves as a postpurification in as far as the customary preparation processes, for example by means of distillation, already afford a purified product.

In this process, liquid or solid piperazine is initially introduced into water in order to obtain an aqueous solution. The subsequent distillative removal of the water is capable of removing the impurities from the piperazine as an azeotrope, which achieves a high color stability and thus makes the piperazine material storable.

The impurities removed in this way are usually components which only impart color later and, at the time at which the product is obtained in modern distillation plants, still exist as colorless "prechromophores" which, depending on the type and duration of the storage, react by condensation and oxidation to give an uncharacterizable mixture of colored compounds. The ultimate trigger for the effect of yellowing is very small amounts of impurities which cannot be detected unambiguously by standard analytical methods in the freshly isolated product.

These impurities appear especially in the MEOA process, since the amination of MEOA is based on ethylene units which enable the formation of C2 fragments by dehydration and deamination under the reaction conditions. These fragments, especially acetaldehyde and more highly condensed subsequent products, cause a lasting deterioration in the product quality, especially the color stability. However, it is also the case here that these impurities generally cannot be detected analytically in the isolated components after the distillation owing to their inhomogeneity and small concentration.

To assess the color stability of the product, this can be determined in long-term storage tests.

The concentration of piperazine dissolved in water can vary widely. Appropriately, the piperazine concentration is so high that no hexahydrate is formed. The concentration is preferably 50% by weight or more, more preferably between 50 and 75% by weight.

The piperazine can be prepared by various processes. Preference is given to the EDC and the MEOA process; particular preference is given to the MEOA process.

In these processes, the synthesis is based on the reaction of ethylene dichloride (EDC) or monoethanolamine (MEOA) with ammonia. Further coproducts of this reaction are, in addition to piperazine, ethylenediamine (EDA), diethylenetriamine (DETA), triethylenetetramine (TETA) and higher linear and cyclic ethylenamines, and also additionally aminoethylethanolamine (AEEA) in the MEOA process.

Irrespective of the choice of process, the purification and separation of the ethylenamine product mix in industrial production is usually effected using a battery of columns in continuous operation. Initially, the ammonia is drawn off in a pressure column, then the process water which is formed (or added in the EDC process) is distilled off.

Afterward, the different ethylenamines are separated distillatively sorted by rising boiling points (sorted by boiling points: EDA, piperazine, MEOA, DETA, AEEA and further higher substances). Alternatively, EDA and piperazine may initially be removed together and separated into the individual components in a downstream column. In this downstream column, EDA is removed overhead and piperazine in the bottom or as a side draw.

Such a column construction may be operated in an optimized manner, in such a way that the individual components are isolated in high purities.

Typically, the degree of purity of the piperazine is more than 90% by weight, preferably above 95% by weight, more preferably more than 99% by weight and most preferably more than 99.9% by weight, before it is used in the process according to the invention.

Thus, the piperazine is preferably obtained from the distillative removal of an ethylenamine product mix or of an EDA/piperazine fraction and fed to the process according to the invention. The piperazine may be introduced into water directly as a fraction effluent (for example as a 65% solution) or be present beforehand as chip material. The chip material is piperazine converted to chip form. The preparation can be effected by cooling drops stemming from a piperazine melt which fall, for example, onto a belt and solidify there into chip form.

The fresh chips obtained in this way may be used in the process according to the invention. It is equally possible to use material which has already been stored and may already have yellowed, in chip form or in another form.

The piperazine isolated after the water has been removed distillatively should have a maximum water content of below 15% by weight, preferably below 5% by weight and more preferably below 1% by weight.

To remove the water, preference is given to carrying out one or more column distillations, in which the water is removed via the top of the column.

Preference is given to effecting a multistage distillative separation. The aqueous piperazine solution is worked up in a distillation unit to give highly pure piperazine at the bottom of the column and water with organic constituents at the top of the column.

Equally, the piperazine may be isolated via a side draw of the purification column.

The distillation unit used may be a column of known design having an evaporator and condenser. The feed is preferably in the upper half of the column, the bottom temperature is preferably from 130 to 170° C., and the pressure at the top of the column preferably from 0.6 to 2 bar. Useful column internals are in principle all common internals, for example trays, structured packings or random packings. Among the trays, preference is given to bubble-cap trays, sieve trays, valve trays, Thormann trays or dual-flow trays; among the random packings preference is given to those having rings, spirals, saddles, Raschig, Intos or Pall rings, barrel or Intalox saddles, Top-Pak, etc., or braids. Preferred structured packings are sheet metal or fabric packings made of metal or plastic. In general, from 10 to 30 theoretical plates are sufficient. The heat is supplied via internal or external heat exchangers of conventional design. The vapors can be condensed at the top of the column using a condenser of conventional design. The top product is preferably fed back to the column as reflux; the preferred reflux ratio is between 1:1 and 4:1.

The isolated piperazine may in turn be obtained as chips or in another form and stored.

The improved color stability may be tested in a long-term test. However, since it is advantageous to test the success of the improved color stability as soon as possible after the isolation, it is a further object of the present invention to provide a rapid test.

This object is achieved by subjecting the isolated piperazine to a heat treatment step and subsequently testing the color change, preferably by means of a color number test.

This assessment is possible shortly after isolation when the product is subjected to the inventive rapid test of aging. To this end, piperazine is heat-treated with the exclusion of air, for example, at 120° C. over 4 h, and its color number is subsequently determined in methanolic or aqueous solution. As a comparison for the long-term behavior, the color number of a freshly prepared piperazine solution may also be determined.

The duration of the heat treatment step and the temperature to be maintained may be varied. They should be in the region of the melting point of piperazine, and a duration of a few hours has been found to be appropriate. The finding of suitable temperature values and heat treatment times is apparent to those skilled in the art in an obvious manner.

In the color number test, the color quality of a compound is generally determined by measuring the transmission of incident light. To this end, the melt or a solution of a known concentration, in a cuvette of known thickness, is passed through by a light beam of a defined wavelength. At a given wavelength, the percentage of the light energy allowed to pass through gives a defined color number. The APHA color scale is appropriate for weakly colored solutions.

The color number is measured in a 50 mm plastic cuvette on a spectrometer calibrated beforehand to the zero point using the water used. The piperazine is weighed in in pulverized form, and care has to be taken that there is no excessive heating as a result of friction. The whole procedure also has to be carried out rapidly in an efficiently ventilated location in order to keep water ingress owing to the hygroscopicity of piperazine low.

Use of this simple analytical technique confirms that on-spec piperazine which is isolated as chips from the melt of the distillative workup have a distinctly poorer color number after heat treatment than before the treatment.

In the context of the present invention, "on-spec" means that the piperazine fulfills the usual commercial requirements on purity, maximum water content and color number. A particularly high standard for on-spec piperazine is, for example, a purity of >99.9% (GC), water content <1% and an APHA color number of ≦30.

In turn, it has been found that piperazine which, after distillative separation, is initially isolated by passing the column effluent into water as a 65% aqueous solution and subsequently drying it by distillation in the process according to the invention has a distinctly better color stability in the rapid test of aging. These results are confirmed in subsequent long-term storage tests.

In addition, it is found that piperazine which is initially isolated as chip material and is transferred into aqueous solution only after storage in on-spec condition, as a result of subsequent distillative drying by the process according to the invention, likewise exhibits improved color stability in the rapid test of aging. These results too are confirmed in long-term tests.

Moreover, it is found that piperazine which is isolated on-spec as chip material and is chemically on-spec but yellowed as a result of prolonged storage and is transferred into aqueous solution, as a result of subsequent distillative drying by the process according to the invention, likewise exhibits the color stability of freshly treated piperazine in the rapid test of aging. These results too are confirmed in long-term tests.

The present invention is illustrated in detail with reference to the example which follows.

EXAMPLE

Dewatering of Aqueous Piperazine Solution

An aqueous piperazine solution is prepared in a stock vessel of 20 liters at a temperature of 65° C. The concentration of the piperazine in the aqueous solution is 68% by weight. A laboratory column (DN 50) having 20 bubble-cap trays made of glass is selected. The feed is to tray 13. The continuous distillation is carried out at a top pressure of 1 bar; the bottom temperature is 150° C. The feed rate is 1100 g/h; 735 g/h of piperazine having a purity of 99.9% by weight are drawn off in the bottom; at the top, water is obtained with a small proportion of piperazine at a rate of 365 g/h. The reflux ratio is 2:1.

Color Number Test

About 1 gram of the pulverized sample is weighed into a bottle having a two-piece screw lid. The weight is noted.

To remove air, the vessel is evacuated and aerated with argon three times each in a desiccator provided with vacuum and argon connection; subsequently, the sample is sealed under an argon stream. Air in the sample necessarily has to be prevented, since oxygen gives rise to color-triggering oxidation products under heat treatment conditions.

To remove air, the vessel may also be blown through with nitrogen over 30 minutes.

The sample vessel is placed fully in a preheated oil bath (or a preheated oven) (120° C.), and stored at constant temperature for 4 h. After the sample has cooled, ten times the mass of water is added in order to dissolve the piperazine.

The following color numbers are determined by this process before and after the heat treatment:

| Anhydrous sample | Color number before heat treatment | Color number after heat treatment |
|---|---|---|
| On-spec piperazine sample (prior art) | 24 APHA | 54 APHA |
| Piperazine sample after inventive isolation | 22 APHA | 25 APHA |

What is claimed is:

1. A process for improving the color stability by postpurifying piperazine, which comprises the following steps:
   preparing an aqueous piperazine solution by introducing solid or liquid piperazine having a degree of purity of at least 90% by weight in water;
   removing the water by distilling;
   isolating the piperazine with a maximum residual content of water of <15% by weight.

2. The process according to claim 1, wherein the solid or liquid piperazine is obtained from a distillative removal of an ethyleneamine product mix or an ethylenediamine-piperazine fraction.

3. The process according to claim 1, wherein the piperazine is introduced into water directly as a fraction effluent.

4. The process according to claim 1, wherein the solid piperazine is present as chip material.

5. The process according to claim 1, wherein the solid or liquid piperazine is obtained from the monoethanolamine (MEOA) process.

6. The process according to claim 1, wherein the solid or liquid piperazine has a degree of purity of >95% by weight.

7. The process according to claim 1, wherein the water is removed by column distillation via the top of the column and wherein the piperazine is isolated from the bottom or via a side draw of the column.

8. The process according to claim 7, wherein the bottom temperature is 130-170° C., the pressure at the top of the column is from 0.6 to 2 bar, the column has from 10 to 30 theoretical plates.

9. The process according to claim 7, wherein the reflux ratio is between 1:1 and 4:1.

10. The process according to claim 1, wherein the isolated piperazine is subjected to a heat treatment step and a color change is subsequently tested.

11. A process for improving the color stability by postpurifying piperazine, which comprises the following steps:
    preparing an aqueous piperazine solution by introducing solid or liquid piperazine having a degree of purity of at least 90% by weight in water;
    removing the water by distilling;
    isolating the piperazine with a predefined maximum residual content of water and the isolated piperazine is subjected to a heat treatment step and a color change is subsequently tested.

12. The process according to claim 1, wherein the solid or liquid piperazine has a degree of purity of >99% by weight.

13. The process according to claim 1, wherein the solid or liquid piperazine has a degree of purity of >99.9% by weight.

14. The process according to claim 1, wherein the isolated piperazine has a maximum residual content of water of <5% by weight.

15. The process according to claim 1, wherein the isolated piperazine has a maximum residual content of water of <1% by weight.

16. The process according to claim 11, wherein the piperazine is introduced into water directly as a fraction effluent.

17. The process according to claim 11, wherein the solid piperazine is present as chip material.

18. The process according to claim 11, wherein the solid or liquid piperazine is obtained from the monoethanolamine (MEOA) process.

19. The process according to claim 11, wherein the solid or liquid piperazine has a degree of purity of >95% by weight and wherein the isolated piperazine has a maximum residual content of water of <5% by weight.

20. The process according to claim 11, wherein the solid or liquid piperazine has a degree of purity of >99.9% by weight and wherein the isolated piperazine has a maximum residual content of water of <1% by weight.

* * * * *